United States Patent [19]

Andrews et al.

[11] Patent Number: 4,976,702
[45] Date of Patent: Dec. 11, 1990

[54] SYRINGE NEEDLE GUARD

[75] Inventors: E. Trent Andrews, San Francisco; Robert R. Moore, Hayward, both of Calif.

[73] Assignee: Serad, Inc., San Francisco, Calif.

[21] Appl. No.: 339,399

[22] Filed: Apr. 17, 1989

[51] Int. Cl.⁵ .............................................. A61M 5/32
[52] U.S. Cl. .................................... 604/198; 604/263
[58] Field of Search ............... 604/198, 263, 195, 192, 604/187

[56] References Cited

U.S. PATENT DOCUMENTS

| 4,631,057 | 12/1986 | Mitchell | 604/198 |
| 4,702,738 | 10/1987 | Spencer | 604/198 |
| 4,723,943 | 2/1988 | Spencer | 604/198 |
| 4,826,491 | 5/1989 | Schramm | 604/198 |

Primary Examiner—John D. Yasko
Attorney, Agent, or Firm—Bielen, Peterson & Lampe

[57] ABSTRACT

A shield for a syringe mounted hypodermic needle which utilizes a translucent sheath. The sheath extends over the barrel to one position adjacent the barrel flange and to another position or beyond the needle point. The sheath may be distinctly stopped at these positions.

3 Claims, 2 Drawing Sheets

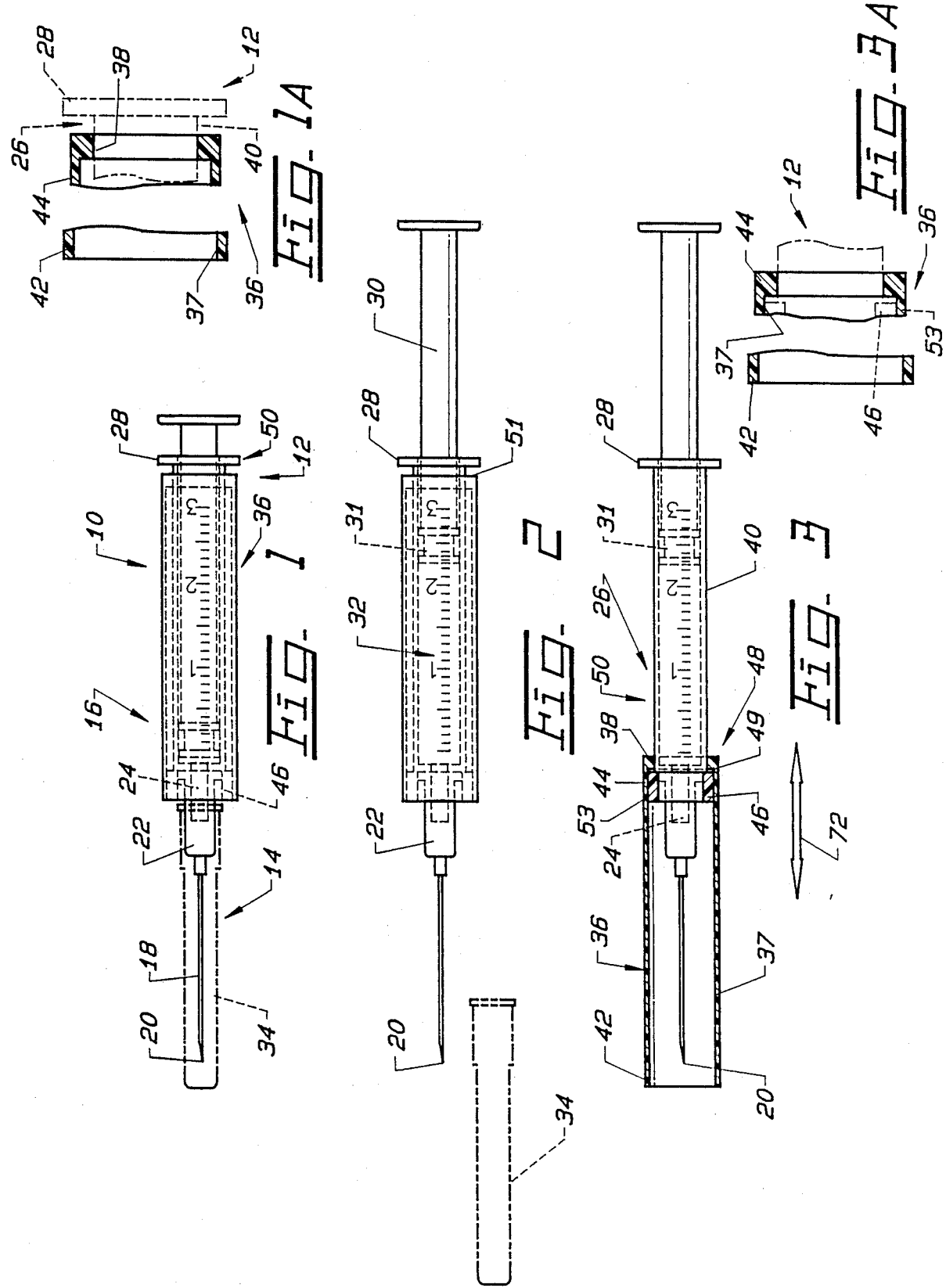

SYRINGE NEEDLE GUARD

BACKGROUND OF THE INVENTION

The present invention relates to a novel shield for a syringe mounted hypodermic needle.

Syringes and hypodermic needles are used very extensively in the medical field to introduce or remove material from the body parenterally. Although hypodermic needles and syringes are quite useful they must be carefully handled by medical practitioners since there is a danger that serious diseases may be spread by an accidental jab from a contaminated hypodermic needle.

In the past, hypodermic needles and syringes have been shipped with a cup which snugly fit over the hub portion of the syringe and extends beyond the end of the hypodermic needle to protect the same. This cap is separable from the needle and syringe combination, and is often lost after initial removal. Also, such cap must be placed on the syringe by exerting force toward the point of the needle. In the past, users have been accidentally pricked by the hypodermic needle when such cap failed to encompass the needle and engage the hub portion of the syringe. Moreover, syringe and needle devices are generally disposable after usage on a single patient. Unfortunately, such discarded syringe and needles have found their way into public areas such as streets, sidewalks, vacant lots, beaches, and the like, causing accidental contact with passersby.

A shield device for a syringe mounted hypodermic needle which overcomes the problems encountered in the prior art would be a great advance in the medical field.

SUMMARY OF THE INVENTION

In accordance with the present invention a novel and useful shield device for a syringe mounted hypodermic needle is herein provided.

The shield of the present invention employs a translucent sheath which extends over the barrel of the hypodermic needle. The sheath is movable relative to the barrel and extendable between the flange end of the syringe barrel and the tip of the syringe. Such, the sheath may be described as extending to a first position adjacent the flange end of the barrel of the syringe and to a second position beyond the point of the hypodermic needle.

Stop means may be provided for limiting movement of the sheath between the flange end of the syringe and the tip end of the syringe. Such stop means may take the form of an obstruction placed at either end of the syringe barrel to engage a portion of the shield.

Means may also be provided in the present invention for holding the sheath in a first extended position adjacent the flange end of the barrel or a second extended position beyond the point of the hypodermic needle. Of course, the latter position would protect the user from being jabbed by the end of the hypodermic needle while handling the needle and syringe. Such holding means may be accomplished by the provision of including a tapered inner wall of the translucent sheath which is engageable with the outer surface of the barrel of the syringe. Such a structure is particularly auspicious when the sheath is extended the point of the tip of the needle i.e. in the second extended position. In this regard, the syringe may be fitted with a collar which permits engagement between the tapered inner wall of the sheath and the syringe body. Further, a groove and cooperating protuberance may be fitted onto the syringe or the sheath. Thus, the syringe may include either a groove or a protuberance respectively engageable by a protuberance or groove on the sheath. In certain cases, a plurality of grooves may be placed on either the sheath or syringe to engage a protuberance on the cooperating body, as the case may be.

It may be apparent that a novel and useful shield device for a needle and syringe has been described.

It is therefore an object of the present invention to provide a shield device for a syringe mounted hypodermic needle which protects the user of the syringe and needle from accidental jabbing or pricking by the hypodermic needle tip.

It is another object of the present invention to provide a shield device for a syringe mounted hypodermic needle which includes a sheath movable along the exterior of the syringe barrel to multiple positions and is not separable from the syringe and hypodermic needle unit.

Another object of the present is to provide a shield device for a syringe mounted hypodermic needle which is easily retrofitted on existing needle and syringe units and on machines for manufacturing for such needle and syringe units.

Yet another object of the present invention is to provide a shield device for a syringe mounted hypodermic needle which is simple and inexpensive to manufacture, permitting disposal with a disposable needle and syringe unit.

A further object of the present invention is to provide a shield device for a syringe mounted hypodermic needle which is safely usable by a medical practitioner requiring a force exerted away from the needle point in order to protect the same.

Another object of the present invention is to provide a shield device for a syringe mounted hypodermic needle which protects the point of a hypodermic needle after disposal of the same.

A further object of the present invention is to provide a shield device for a syringe mounted hypodermic needle which does not interfere with the visual acquiring of measurement data and indicia appearing on the external surface of a syringe barrel.

Yet another object of the present invention is to provide a shield device for a syringe mounted hypodermic needle which prevents the spread of diseases.

The invention possesses other objects and advantages especially as concerns particular character characteristics and features thereof which will become apparent as the specification continues.

BRIEF DESCRIPTION OF THE DRAWINGS

FIG. 1 is a front elevational view showing an embodiment of the present on a needle and syringe unit, as well as a prior art cap, shown in phantom.

FIG. 1A is broken, sectional, enlarged view of the needle and syringe unit depicted in FIG. 1.

FIG. 2 is a side elevational view depicting the partial operation of the embodiment depicted in FIG. 1 with the prior art cap removed and shown in phantom.

FIG. 3 is a side view of the needle and syringe unit depicted in FIGS. 1 and 2 with the shield device depicted in section.

FIG. 3A is a broken, sectional, enlarged view of the needle and syringe unit depicted in FIG. 3.

Figure 4:
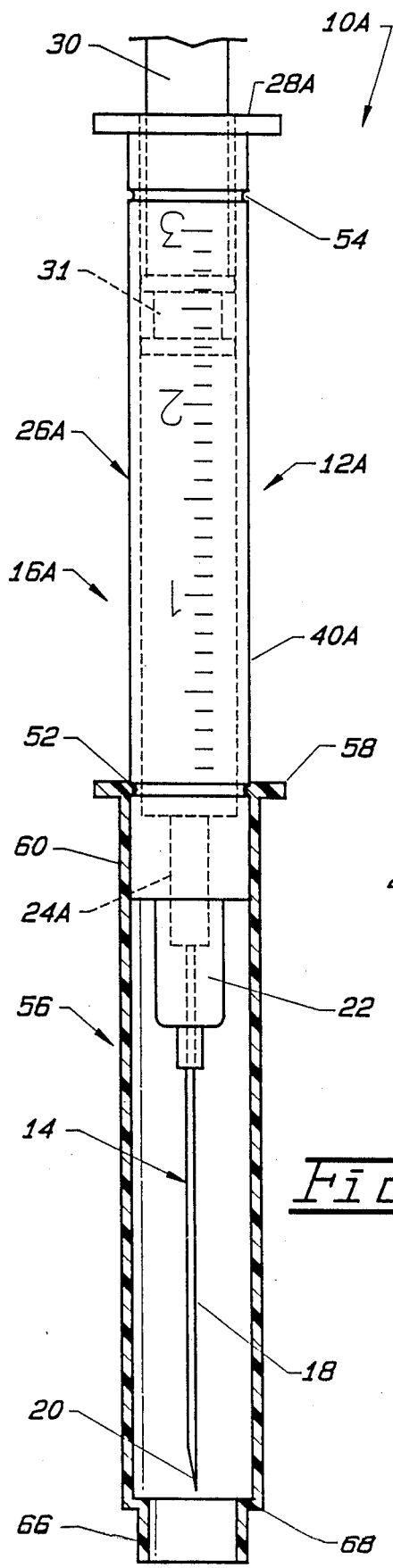
FIG. 4 is a side elevational view of a needle and syringe unit depicting another embodiment of the present invention in section.

For a better understanding of the invention reference is made to the following detailed description of the preferred embodiments thereof which should be referenced to the hereinabove described drawings.

DETAILED DESCRIPTION OF THE PREFERRED EMBODIMENTS

The embodiment of the invention as a whole depicted in the drawings by reference characters 10 and 10A. FIGS. 1-3 illustrate shield device 10 which is usable with syringe 12 and hypodermic needle 14, forming a unit 16.

Hypodermic needle 14 includes a hollow cannula 18 with a ground point 20. A hub 22 connects to cannula 18 opposite to points 20 of cannula 18. Hub 22 may or may not detachably fit to the tip 24 of syringe 12. Tip 24 lies at one end of syringe barrel 26, best shown in FIG. 3. A flange 28 lies at the other end of barrel 28 from tip 24. A piston or plunger 30 closely fits the interior of barrel 26 to draw liquids therein and to force liquids out of the interior of barrel 26. It should be noted that the end of piston 30 includes an elastomeric seal 31. Indicia 32 depict the volumetric level of the liquid which may be found in barrel 26 of syringe 12.

Also shown on FIGS. 1 and 2 is a cap 34 which is intended to friction fit to the exterior of hub 22 in order to protect the integrity of point 20 and to prevent jabbing or pricking by point 20 during handling of unit 16. As depicted in FIG. 2, cap 20 has been removed from unit 16. To replace cap 34 over point 20 of cannula 18 would require a motion toward point 20. In the past, this motion has resulted in accidental jabbings by point 20 to someone handling unit 16. In addition, it should be apparent that cap 34 is completely separable from unit 16 and may easily be lost or damaged to the extent that it is not reusable to cover point 20 of cannula 18.

Shield device 10 is depicted in one embodiment, FIGS. 1-3 as including a translucent sheath 36 in the form of a cylindrical body which lies over syringe barrel 26. Translucent sheath 36 may be formed of plastic, glass, or any suitable material compatible with the medical use for unit 16. Sheath 36 includes a flange end 38 which closely fits over the exterior surface 40 of barrel 26. The interior surface 37 of sheath 36 slightly tapers from a large transverse dimension end 42 to a smaller transverse dimension end 44, adjacent flange FIGS. 1A and 3A 38.

Shield device 10 also includes a collar 46 which is friction fitted or formed intergrally with hub 22 of needle 14 or with the tip end of syringe 12. Thus, sheath 36 is extendable to a first position over barrel 26 adjacent flange 28 of syringe 12 and to a second position beyond the point 20 of hypodermic needle 14, FIG. 1 and 3, respectively. The small diameter end 44 of shield 36 frictionally engages the exterior surface 53 of collar 46 in the extended position depicted in FIG. 3. Thus, stop means 48 is provided for limiting the movement of sheath 36 between the flange 28 of syringe 12 and the tip 24 of syringe 12. Such stop means 48 may take the form of contact between the inner transverse surface 46 of flange 38 and collar 46, as well as contact between the outer transverse surface 51 of flange 38 and flange 28 of syringe 12. It should also be observed, that the outer surface 40 of syringe barrel 26 slightly tapers to a large transverse dimension to adjacent flange 28 of barrel 26 and to a smaller transverse dimension adjacent tip 22. Thus, the interaction of the outer surface 53 of collar 46 with the interior surface 37 of the small end 44 of sheath 36, FIG. 3 and 3A, and the interaction of flange 38 with the exterior surface 40 of barrel 26, FIG. 1 and 1A serve as holding means 50 to maintain sheath in either of the extended positions depicted, therein. In addition, such interactions may also serve as stop means 48 hereinabove described.

Figure 5:
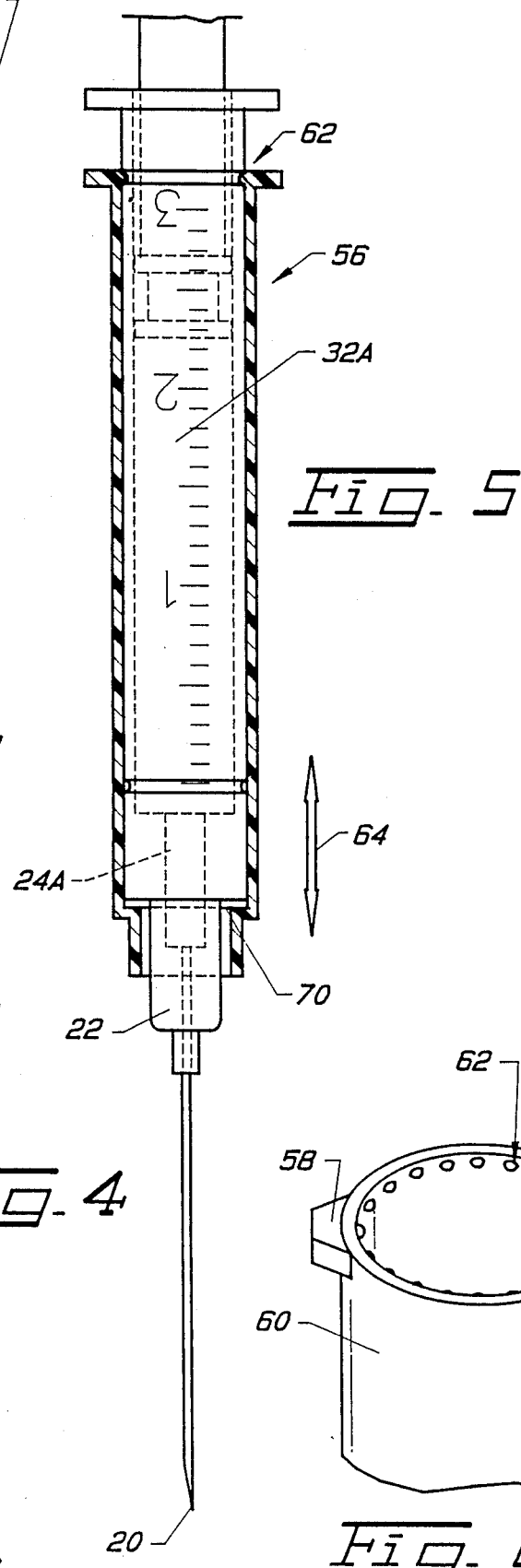
FIG. 5 is a side elevational view of the embodiment of the present invention depicted in FIG. 4 showing the sheath member in one of its extended positions.
Figure 6:
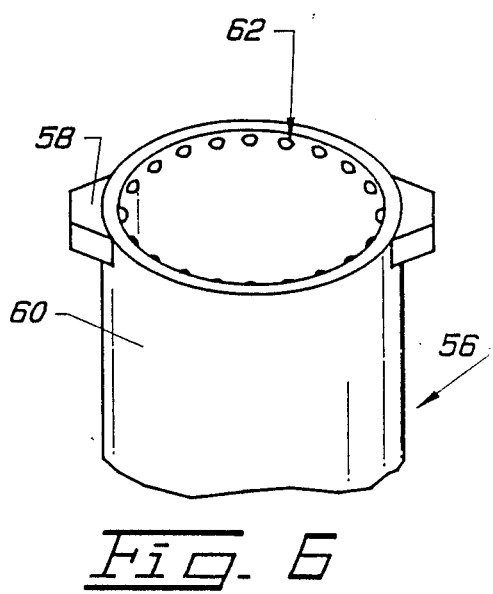
FIG. 6 is a top partial isometric view of a portion of the sheath depicting an embodiment of a protuberance on its inner surface.

Turning to FIGS. 4-6, a syringe 12A is depicted having piston 30 (partially illustrated) which fits within a barrel 26A. The outer surface 40A of barrel 26A includes a pair of circumferential grooves 52 and 54.

Sheath 56 is formed with a flange 58 at end portion 60. A plurality of protuberances 62 extend inwardly at flange 58 and are capable of stopping and holding sheath 56 along its travel, shown by directional arrow 64, at grooves 52 and 54, FIGS. 4 and 5, respectively. As may be apparent from FIGS. 4 and 5, the holding of sheath 56 in such positions either exposes hypodermic needle 14 for use or covers the same when hypodermic needle 14 is not in use or to be disposed. Stepped down portion 66 of sheath 56 includes a shoulder 68 which may ride against end surface 70 of barrel 26A. Since sheath 56 is translucent, indicia 32A are clearly visible when covering barrel 26A.

In operation, the user of shield device 10 would retract sheath 36 to the position shown in FIG. 1. The interaction of flange 38 of sheath 36 and the exterior surface 40 of barrel 26 would stop any further movement of sheath 36 toward flange 28 of syringe 12. Needle and syringe unit 16 may be used in the conventional manner at this point by the movement of plunger 30 depicted in FIG. 2. After use or before reuse, in certain cases, sheath 36 would be extended into the position depicted in FIG. 3. The interaction of flange 38 of sheath 36 and collar 46 would stop and hold sheath 36 in the position shown in FIG. 3. It should be noted that the movement required of sheath 36 to achieve this position is opposite the direction which would normally permit point 20 of hypodermic needle 18 to jab or prick the user. The application or force on sheath 36 back toward flange 28 of syringe 12 would free sheath 36 for such travel for holding and stopping sheath 36, again, in the position shown in FIG. 1. With reference to the embodiment 10A depicted in FIGS. 4-6, the user would simply move sheath 56 from the position depicted in FIG. 4 to the position depicted in FIG. 5. The interaction of protuberances 62 and grooves 52 and 54 would stop and hold sheath 56 in the positions shown. It should be noted, that in either embodiment the stopping and holding of sheaths 36 and 56 is a temporary condition. The application of force along directional arrows 64 or 72 would easily free sheaths 36 and 56 from any of the extended position shown in FIGS. 1-5.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A shield device for a syringe mounted pointed hypodermic needle the, syringe including a barrel with indicia, the barrel having a tip end to accommodate the needle, and a flange end providing an opening for a piston comprising:
   a. a translucent sheath said translucent sheath including a tapered inner wall forming a large end having a large transverse dimension and small end having a small transverse dimension, said sheath being extendable to a first position over the barrel adjacent the flange end of the barrel, said sheath being movable relative to the barrel and being extendable to a second position beyond the point of hypodermic needle;
   b. stop means for limiting movement of said sheath between the flange end of the syringe and the tip end of the syringe.
   c. means for holding said sheath in said first extended position adjacent the flange end of the barrel, said means for holding said first extended position comprising a flange extending inwardly from said small end of said translucent sheath, said flange including a surface which frictionally engages the barrel adjacent the flange end of the barrel; and
   d. means for holding said sheath in said second position beyond the point of the hypodermic needle comprising a collar circumjacently positioned relative to the barrel adjacent the tip end, said collar including an outer surface frictionally engaging said tapered inner surface of said sheath at said small end thereof.

2. The shield device of claim 1 in which said stop means includes said flange frictionally engaging the barrel adjacent the flange end of the barrel.

3. The shield device of claim 1 in which said stop means includes said outer surface of said collar frictionally engaging said tapered inner surface of said sheath at said small end thereof.

* * * * *